(12) United States Patent
Rucker et al.

(10) Patent No.: US 11,964,387 B2
(45) Date of Patent: Apr. 23, 2024

(54) METHODS FOR IMPROVING STABILITY OF CONCENTRIC TUBE STEERABLE DEVICES USING ASYMMETRIC FLEXURAL RIGIDITY

(71) Applicants: University of Tennessee Research Foundation, Knoxville, TN (US); Hunter Bryant Gilbert, Baton Rouge, LA (US)

(72) Inventors: Daniel Caleb Rucker, Knoxville, TN (US); Hunter Bryant Gilbert, Baton Rouge, LA (US)

(73) Assignees: University of Tennessee Research Foundation, Knoxville, TN (US); Board of Supervisors of Louisiana State University and Agricultural and Mechanical College, Baton Rouge, LA (US)

( * ) Notice: Subject to any disclaimer, the term of this patent is extended or adjusted under 35 U.S.C. 154(b) by 14 days.

(21) Appl. No.: 17/848,970

(22) Filed: Jun. 24, 2022

(65) Prior Publication Data
US 2023/0025383 A1 Jan. 26, 2023

Related U.S. Application Data

(60) Provisional application No. 63/214,922, filed on Jun. 25, 2021.

(51) Int. Cl.
*B25J 18/06* (2006.01)
*A61B 17/00* (2006.01)
(Continued)

(52) U.S. Cl.
CPC .......... *B25J 18/06* (2013.01); *A61B 17/00234* (2013.01); *A61B 34/30* (2016.02);
(Continued)

(58) Field of Classification Search
CPC ...... B25J 18/002; B25J 18/005; B25J 18/025; B25J 18/04; B25J 18/06; A61B 17/00234;
(Continued)

(56) References Cited

U.S. PATENT DOCUMENTS

| | | | |
|---|---|---|---|
| 4,900,218 A * | 2/1990 | Sutherland | ............... B25J 18/06 |
| | | | 901/22 |
| 7,959,634 B2 * | 6/2011 | Sennett | .............. A61B 17/1604 |
| | | | 606/79 |

(Continued)

FOREIGN PATENT DOCUMENTS

| | | | | |
|---|---|---|---|---|
| WO | WO-2022161266 A1 * | 8/2022 | ........... | A61B 1/0011 |
| WO | WO-2023076667 A1 * | 5/2023 | | |

OTHER PUBLICATIONS

Azimian, H. et al., "Structurally-Redesigned Concentric-Tube Manipulators With Improved Stability", IEEE/RSJ International Conference on Intelligent Robots and Systems, Sep. 14-18, 2014, 6 pages.

(Continued)

*Primary Examiner* — Adam D Rogers
(74) *Attorney, Agent, or Firm* — Stanek Lemon Crouse & Meeks, P.A.

(57) ABSTRACT

A concentric tube steerable device includes a plurality of tubes having a nested, concentric configuration. The tubes include an outer tube and an inner tube that extends coaxially within the outer tube. The inner tube terminates at a tip, and a pose of the tip is effectuated through individual or collective rotation or translation of the tubes about a tube axis. The concentric tube steerable device includes an actuator for rotating at least one tube about a respective tube axis, and a translator for translating at least one tube along a respective tube axis. Each tube includes a precurved portion and a corresponding axis of precurvature. For at least one tube, a flexural rigidity of the tube along its axis of precurvature is less than a flexural rigidity of the tube along a (Continued)

second axis that is perpendicular to the axis of precurvature, thereby improving stability of the tube.

19 Claims, 8 Drawing Sheets

(51) Int. Cl.
| | |
|---|---|
| *A61B 34/00* | (2016.01) |
| *A61B 34/30* | (2016.01) |
| *B25J 18/00* | (2006.01) |
| *B25J 18/02* | (2006.01) |
| *B25J 18/04* | (2006.01) |

(52) U.S. Cl.
CPC .............. *A61B 34/70* (2016.02); *B25J 18/002* (2013.01); *B25J 18/005* (2013.01); *B25J 18/025* (2013.01); *B25J 18/04* (2013.01); *A61B 2017/00309* (2013.01); *A61B 2017/00331* (2013.01); *A61B 2017/00991* (2013.01); *A61B 2034/301* (2016.02)

(58) Field of Classification Search
CPC ................... A61B 34/30; A61B 34/70; A61B 2017/00309; A61B 2017/00331; A61B 2017/00991; A61B 2034/301
See application file for complete search history.

(56) References Cited

U.S. PATENT DOCUMENTS

| | | | | |
|---|---|---|---|---|
| 8,551,021 | B2* | 10/2013 | Voeller .............. | A61M 25/0013 600/585 |
| 8,708,953 | B2* | 4/2014 | Salahieh ................ | A61B 90/10 604/95.01 |
| 9,216,057 | B2* | 12/2015 | Goshayeshgar ... | A61B 18/1492 |
| 10,420,537 | B2* | 9/2019 | Salahieh .......... | A61B 17/00234 |
| 10,441,371 | B2* | 10/2019 | Hendrick ........... | A61B 1/00101 |
| 11,723,738 | B2* | 8/2023 | Riojas .................... | A61B 34/72 606/1 |
| 2008/0071288 | A1* | 3/2008 | Larkin ............... | A61B 1/00165 901/14 |
| 2014/0309587 | A1* | 10/2014 | Kim ..................... | B23K 26/361 219/121.72 |
| 2016/0346513 | A1* | 12/2016 | Swaney ............. | A61B 17/3417 |

OTHER PUBLICATIONS

Chen, Shengwei et al., "Towards the design of mechanically superior tubular structures for microcatheters", Smart Mater. Struct. 28 (2019), 13 pages.

Childs, Jake A. et al., "Concentric Precurved Bellows: New Bending Actuators for Soft Robots", IEEE Robotics And Automation Letters, vol. 5, No. 2, Apr. 2020, 8 pages.

Gilbert, Hunter B. et al., "Elastic Stability of Concentric Tube Robots: A Stability Measure and Design Test", IEEE Transactions on Robotics, vol. 32, No. 1, Feb. 2026, 16 pages.

Girard, Cedric et al., "Design of Concentric Tube Robots Using Tube Patterning for Follow-The-Leader Deployment", Journal of Mechanisms and Robotics, vol. 13, Feb. 2021, 8 pages.

Hur, Jeong Min et al., "Harnessing distinct deformation modes of auxetic patterns for stiffness design of tubular structures", Materials and Designs 198 (2021), 6 pages.

Kim, Ji-Suk et al., "Toward a Solution to the Snapping Problem in a Concentric-Tube Continuum Robot: Groved Tubes with Anisotropy", IEEE International Conference on Robotic & Automation, 2021, 6 pages.

Kim, Jongwoo et al., "A Needlescopic Wrist Mechanism With Articulated Motion and Kinematic Tractability for Micro Laparoscopic Surgery", IEEE/ASME Transactions On Mechatronics, vol. 25, No. 1, Feb. 2020, 10 pages.

Kim, Jongwoo et al., "Continuously Variable Stiffness Mechanism Using Nonuniform Patterns on Coaxial Tubes for Continuum Microsurgical Robot", IEEE Transactions on Robotics, vol. 35, No. 6, Dec. 2019, 13 pages.

Kutzer, Michael D.M. et al., "Design of a New Cable-Driven Manipulator with a Large Open Lumen: Preliminary Applications in the Minimally-Invasive Removal of Osteolysis", IEEE International Conference on Robotics and Automation, 2011, 8 pages.

Lee, Dae-Young et al., "Anistropic Patterning to Reduce Instability of Concentric-Tube Robots", IEEE Transactions on Robotics, vol. 31, No. 6, Dec. 2015, 13 pages.

Luo, Kevin Ai Xin Jue et al., "Designing Concentric Tube Manipulators for Stability Using Topology Optimization", IEEE/RSJ International Conference on Intelligent Robots and Systems, Madrid, Spain, Oct. 2018, 6 pages.

Luo, Kevin Ai Xin Jue et al., "Design Optimization for the Stability of Concentric Tube Robots", IEEE Robotics And Automation Letters, vol. 6., No. 4, Oct. 2021, 8 pages.

* cited by examiner

METHODS FOR IMPROVING STABILITY OF CONCENTRIC TUBE STEERABLE DEVICES USING ASYMMETRIC FLEXURAL RIGIDITY

CROSS-REFERENCE TO RELATED APPLICATION

The present application claims the benefit of and priority to U.S. Provisional Patent Application No. 63/214,922, filed Jun. 25, 2021, the contents of which is hereby incorporated herein as set forth in its entirety.

STATEMENT OF GOVERNMENT SUPPORT

This invention was made with government support under Grant No. A18-0040 (Award #1652588) by the National Science Foundation. The government has certain rights in the invention.

FIELD

The inventive concept relates generally to concentric tube steerable devices and, more particularly, to using asymmetric flexural rigidity to improve stability in concentric tube steerable devices.

BACKGROUND

Concentric tube steerable devices (e.g., concentric tube robots or CTRs) are often catheter-sized and well suited for minimally invasive surgery inside confined body cavities. These devices are often composed of sets of nested, precurved concentric tubes and are capable of assuming complex three-dimensional (3D) curves. The family of 3D curves that a concentric tube steerable device can assume can depend on the number, curvatures, or lengths of the tubes in its tube set. In addition, the stability, stiffness, and strength of the concentric tube steerable device can significantly affect the allowable range of bending angles. Improvements in stability, stiffness, and strength are therefore desirable.

SUMMARY

The following disclosure describes non-limiting examples of some embodiments. For instance, other embodiments of the disclosed systems and methods may or may not include the features described herein. Moreover, disclosed advantages and benefits can apply only to certain cases of the invention and should not be used to limit the disclosure. The embodiments disclosed herein each have several aspects no single one of which is solely responsible for the disclosure's desirable attributes.

The present disclosure describes a concentric tube steerable device. The device includes a plurality of tubes having a nested, concentric configuration. The plurality of tubes includes an outer tube and an inner tube that extends coaxially within the outer tube. The inner tube terminates at a distal tip. A pose of the distal tip is effectuated through individual or collective rotation or translation of the plurality of tubes about a tube axis. The device includes at least one actuator for rotating at least one tube of the plurality of tubes about a respective tube axis and/or translating at least one tube of the plurality of tubes along a respective tube axis. Each tube of the plurality of tubes includes a precurved portion and corresponding axis of precurvature. A flexural rigidity of a particular tube along its axis of precurvature is less than a flexural rigidity of the particular tube along a second axis that is perpendicular to the axis of precurvature.

The device of the previous paragraph can include any one or more of the following features or any of the features described herein. A ratio of the flexural rigidity along the axis of precurvature to the flexural rigidity along the second axis can be less than 0.8, such as about 0.5. A ratio of the flexural rigidity along the axis of precurvature to the flexural rigidity along the second axis can be less than a sum of 1 plus an effective Poisson's ratio (e.g., approximately 1.35) of a material of the particular tube. A ratio of the flexural rigidity along the axis of precurvature square over the torsional rigidity times the flexural rigidity along the second axis, $$\left(\frac{(EI_x)^2}{GJ * EI_y}\right),$$

can be less than a sum of 1 plus an effective Poisson's ratio of a material of the particular tube. A flexural rigidity of the particular tube along its axis of precurvature can be lower than a torsional rigidity of the particular tube.

The device of any of the preceding paragraphs can include any combination of the features of this paragraph or any of the features described herein. A first tube of the plurality of tubes can include a plurality of slots. A presence of the plurality of slots can introduce asymmetric stiffness properties in the first tube including a lower flexural rigidity of the first tube along its axis of precurvature relative to the flexural rigidity of the first tube along its second axis. The plurality of slots can include a first set of slots and a second sets of slots are located opposite the first set of slots. Each of the plurality of slots can be proximate a plane corresponding to the axis of precurvature. In some cases, no slot can be located proximate a plane corresponding to the second axis. The plurality of slots can include an interleaved series of slots along a length of the first tube. Each slot can include a substantially rectangular shape, and wherein the longest edge of each slot can be perpendicular to a longitudinal axis of the first tube. First portions of the first tube are thinner than second portions of the first tube. A difference in thickness between the first portions and the second portions can introduce asymmetric stiffness properties in the first tube including a reduction in the flexural rigidity of the first tube along its axis of precurvature relative to the flexural rigidity of the first tube along its second axis. The first portions are located on opposite facing sides of the first tube, proximate a plane corresponding to the axis of precurvature. First portions of the first tube can be composed of a first material. Second portions of the first tube can be composed of a second material. A difference in structural characteristics between the first material and the second material introduces asymmetric stiffness properties in the first tube can include a reduction in the flexural rigidity of the first tube along its axis of precurvature relative to the flexural rigidity of the first tube along its second axis. The first portions are located on opposite facing sides of the first tube, proximate a plane corresponding to the axis of precurvature.

A concentric tube steerable device can include an outer tube. The outer tube can include a precurved portion, a first plurality of discrete openings, and a second plurality of discrete openings. The precurved portion can be defined by an axis of precurvature. The first plurality of discrete openings can be distributed along a first side of the outer tube.

The second plurality of discrete openings can be distributed along a second side of the outer tube. The second side can be opposite the first side. The first plurality of discrete openings and the second plurality of discrete openings introduce asymmetric stiffness properties in the outer tube can include a lower flexural rigidity of the outer tube along the axis of precurvature relative to a flexural rigidity of the outer tube along a second axis that can be perpendicular to the axis of precurvature. The concentric tube steerable device can include an inner tube. The inner tube can be nested and extends coaxially within the outer tube, the inner tube terminating at a distal tip. A pose of the distal tip can be effectuated through individual or collective rotation or translation of the outer tube and/or the inner tube. The concentric tube steerable device can include an actuator for rotating at least one of the outer tube or the inner tube about a respective tube axis and/or for translating at least one of the outer tube or the inner tube along a respective tube axis.

The device of the previous paragraph can include any one or more of the following features or any of the features described herein. A ratio of the flexural rigidity along the axis of precurvature to the flexural rigidity along the second axis can be less 0.8. The asymmetric stiffness properties can include a reduction in the flexural rigidity of the outer tube along its axis of precurvature relative to a torsional rigidity of the outer tube. The inner tube can include a precurved portion. The precurved portion of the inner tube can be defined by an axis of precurvature. A ratio of a flexural rigidity of the inner tube along its axis of precurvature to a flexural rigidity of the inner tube along a second axis that can be perpendicular to the axis of precurvature can be approximately 1. The inner tube can include a precurved portion. The precurved portion of the inner tube can be defined by an axis of precurvature. A ratio of a flexural rigidity of the inner tube along its axis of precurvature to a flexural rigidity of the inner to along a second axis that can be perpendicular to the axis of precurvature can be approximately 0.5.

DETAILED DESCRIPTION

Figure 1:
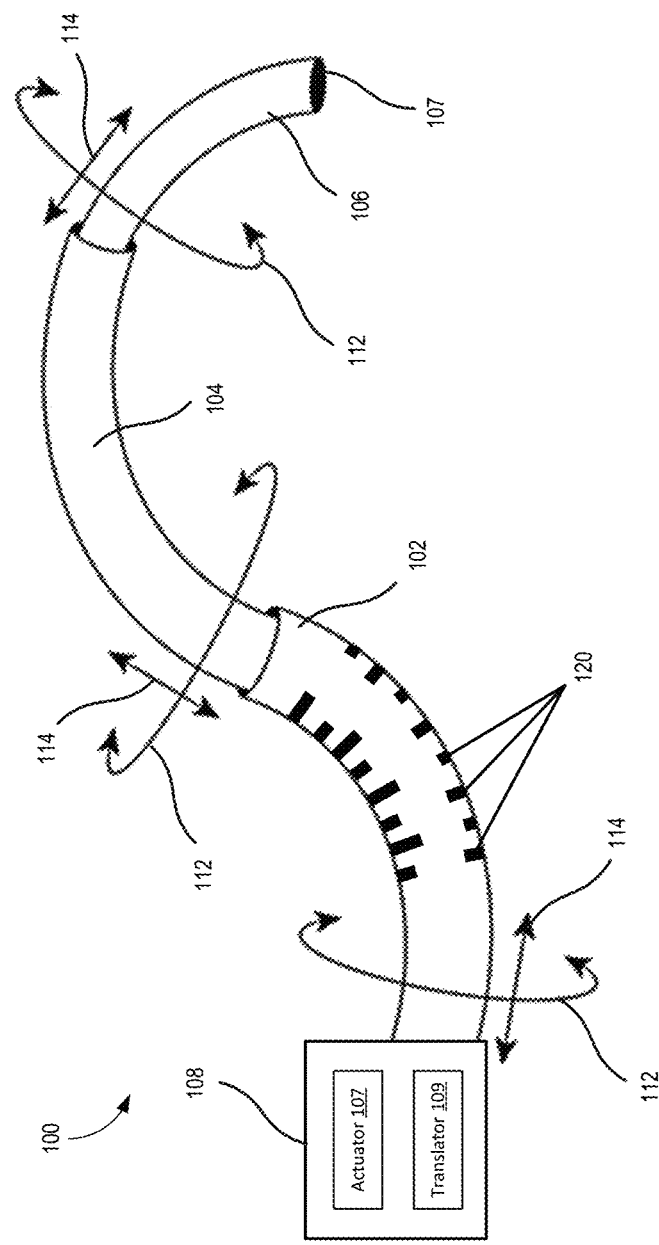
FIG. 1 illustrates a concentric tube steerable device that includes a tube having asymmetric flexural rigidity.

Although certain embodiments and examples are described below, it will be understood that the disclosure extends beyond the specifically disclosed embodiments and/or uses and obvious modifications and equivalents thereof. Thus, it is intended that the scope of the disclosure herein disclosed should not be limited by any particular embodiments described below.

As used herein, the terms "precurved" or "precurved tube" refers to an intentional curvature set into the tube that causes at least a portion of the tube to retain a curved profile at a rest state. In some cases, a tube can be considered precurved if a tube centerline has non-zero curvature somewhere along its length. In some cases, a tube can be considered precurved if an angular variation in a tangent vector is more than one degree.

As used herein, the terms "axis," "device axis," "tube axis," or "longitudinal axis," used in conjunction with the concentric tube steerable devices refers to a line that is centered within and follows a curved configuration of the tubes. For example, because the tubes of a concentric tube steerable device are coaxial in nature, the axis of a concentric tube steerable device can be considered to be centered within and follow the curved configuration of the tubes. Thus, as the curved configuration of the tubes change, the axis can remain centered in the tubes and follow the curved configuration.

As used herein, the term "flexural rigidity" or "EI" refers to a force couple required to bend a fixed non-rigid structure (e.g., a precurved tube) by one unit of curvature. As used herein, the term "torsional rigidity" or "GJ" refers to a torque required to deform a structure (e.g., a precurved tube) by one unit of torsion.

As used herein, the term "pose" is a broad term encompassing its plain and ordinary meaning and may refer to, without limitation, position, orientation, the combination of position and orientation, or any other appropriate location information.

Overview

Conventional techniques for improving stability in concentric tube steerable devices often attempt to reduce the flexural rigidity (EI) relative the torsional rigidity (GJ), for a given tube. By reducing the ratio of the flexural rigidity to the torsional rigidity, $$\left(\frac{EI}{GJ}\right),$$

higher bending angles and improved stability can be achieved. However, such techniques often reduce the EI itself, which can undesirably result in a substantial reduction in bending stiffness, consequently weakening the device's capacity to apply or resist forces.

To address these or other challenges, techniques disclosed herein include structural modifications or implementations to the tube that introduce asymmetric flexural rigidity. In particular, asymmetric (e.g., direction-dependent) flexural rigidity can be achieved by introducing structural characteristics to a tube that reduce the flexural rigidity of a tube along a precurvature axis ($EI_x$) relative to the flexural rigidity perpendicular to the precurvature axis ($EI_y$) (sometimes referred to as the off-axis flexural rigidity or Perpendicular axis). In some cases, the techniques reduce $EI_x$ while reducing $EI_y$ and GJ far less. By introducing the asymmetric flexural rigidity in this way, the techniques can advantageously achieve improved device stability while preserving much of the device's strength, out-of-plane load capacity, and capacity to apply or resist forces.

INTRODUCTION

A concentric tube steerable device (e.g., a concentric tube robot, an active cannula) can be implemented as a slender manipulator composed of two or more precurved elastic tubes nested together. Axial rotation and translation of the tube bases by actuators causes the tubes to bend and twist one another, which changes the collective shape of the tubes and moves the tip through space. This can create a highly miniaturizable device that is potentially useful in minimally invasive surgical applications to navigate through tight spaces and deliver therapy.

The elastic stability of any concentric tube steerable device can be an important consideration. A so-called "snapping" instability can happen when two tubes with overlapping curved regions are rotated with respect to each other. The tubes reach a point where much of the stored elastic energy suddenly releases, and the tubes "snap" to a new configuration with high velocity. The existence of such unstable events limits a concentric tube steerable device's workspace and implies the existence of multiple solutions to the forward kinematics equations, thus complicating modeling and control. As a result, a number of tests have been developed to determine if particular configurations and designs will be stable.

Though some have proposed ways to harness the snapping transitions for useful purposes, much recent concentric tube steerable device research has focused on avoiding unstable behavior by planning and controlling the device to follow stable actuation trajectories, or by designing the tube precurvatures and overlap regions such that instabilities are not present for any motion in the configuration space.

In the development of a standard concentric tube steerable device mechanics model and its analytical solution in the two-tube case, the relationships in Equations (1) and (2) below relate to the stability of the entire rotation space of two tubes with constant precurvature, where L is the overlapped length, $EI_i$ is the flexural rigidity, $GJ_i$ is the torsional rigidity, and $k_i$ is the precurvature of the $i^{th}$ tube.

$$L^2 c < \frac{q^2}{4} \qquad \text{Equation (1)}$$

$$c = k_1 k_2 \frac{EI_1 EI_2 (GJ_1 + GJ_2)}{(EI_1 + EI_2) GJ_1 GJ_2} \qquad \text{Equation (2)}$$

If the two tubes have identical stiffnesses and precurvatures (a usually impractical case, but useful for gaining insight) then the stability condition can reduce to:

$$L^2 K^2 \frac{EI}{GJ} < \frac{q^2}{4} \qquad \text{Equation (3)}$$

This observation inspired further research on potential ways to reduce the effective ratio of flexural rigidity (EI) to torsional rigidity (GJ) for a given tube, so that devices would be capable of higher bending angles (β=κL) and remain stable over the whole rotation space. Conventional techniques attempt to reduce the effective $$\frac{EI}{GJ}$$

ratio. However, such techniques also reduce EI itself by a much greater degree. These results demonstrate that a primary trade-off inherent to structural modification is the drastic reduction in bending stiffness required to achieve sufficient stability improvement, which consequently weakens the device's capacity to apply or resist forces.

Embodiments of the present inventive concept provide an improved approach to concentric tube steerable device stability in which this trade-off is far less severe. In particular, by selectively weakening a tube's flexural rigidities in an asymmetric manner (e.g., reducing the flexural rigidity about the axis of precurvature more ($EI_x$) than the rigidity perpendicular to the precurvature axis ($EI_y$)), the embodiments disclosed herein improve the stiffness/stability trade-off.

A short summary of the equations of the standard concentric tube steerable device mechanics model with external loading is discussed herein, but without applying the typical assumption that $EI_x = EI_y$. Each tube in a concentric tube steerable device obeys the static equilibrium conditions for a Cosserat rod:

$$\dot{n}_i + f_i = 0 \qquad \text{Equation (4)}$$

$$\dot{m}_i + \dot{p}_i \times n_i + l_i = 0 \qquad \text{Equation (5)}$$

and the kinematic equations:

$$\dot{p}_i = R_i e_3 \qquad \text{Equation (6)}$$

$$\dot{R}_i = R_i \hat{u}_i \qquad \text{Equation (7)}$$

where the subscript i denotes the tube index, $m_i: \mathbb{R} \to \mathbb{R}^3$ is the tube's internal moment, $l_i: \mathbb{R} \to \mathbb{R}^3$ is an external distributed moment, $m_i: \mathbb{R} \to \mathbb{R}^3$ is the internal force, $f_i: \mathbb{R} \to \mathbb{R}^3$ is an external distributed force pi: $\mathbb{R} \to \mathbb{R}^3$ is the position, $R_i: \mathbb{R} \to SO(3)$ is the orientation, and $e_3 = [0\ 0\ 1]^T$. All variables are functions of the reference arc length s ∈ [0 L] along the tube centerline. The denotes a derivative with respect to s, and ˆ: $\mathbb{R}^3 \to so(3)$ denotes the standard skew-symmetric form of a vector.

A linear constitutive law relates the kinematics to the statics as $$m_i = R_i K_i (u_i - u_i^*) \qquad \text{Equation (8)}$$

where $K_i = \text{diag}(EI_{xi}, EI_{yi}, GJ_i)$ and $u_i^*$ is the precurvature vector in the unstressed state. Note that it is assumed that $K_i$ is diagonal without loss of generalization because the initial reference frame $R_i^*(s)$ can be attached such that the x and y axes align with the effective principal axes at s. This can be done even if the principal axes vary along the length, which would entail a $u^*(s)$ with nonzero torsional component. The constitutive law can be differentiated and substituted. Then isolating the torsional component (by multiplying by $e_3^T R_i$), you get:

$$\dot{u}_{iz} = u_{iz}^* - e_3^T K_i^{-1} (\hat{u}_i K_i + \dot{K}_i)(u_i - u_i^*) \qquad \text{Equation (9)}$$

where $e_3^T R_i l_i = 0$ under the assumption of no torsional friction. Note that Equation (9) was simplified in all prior work by assuming $EI_x = EI_y$, but embodiments of the present inventive concept intentionally do not make that assumption, so Equation (9) is left in its general form.

The x and y components of the tube curvature $u_i$ are related to the curvature $u = [u_x\ u_y\ 0]^T$ of a Bishop frame R that slides along the device centerline with no torsion:

$$\dot{R} = R\hat{u} \qquad \text{Equation (10)}$$

$$\dot{p} = Re_3 \qquad \text{Equation (11)}$$

Based on the concentric constraint $\dot{p}_i = \dot{p}$:

$$R_i = R \begin{bmatrix} \cos\psi_i & -\sin\psi_i & 0 \\ \sin\psi_i & \cos\psi_i & 0 \\ 0 & 0 & 2 \end{bmatrix} = R \begin{bmatrix} R_{\psi i} & 0_{2\times 1} \\ 0_{1\times 2} & 1 \end{bmatrix} \quad \text{Equation (12)}$$

And the curvature relationship is then:

$$\begin{bmatrix} U_{ix} \\ U_{iy} \end{bmatrix} = R_{\psi i}^T \begin{bmatrix} u_x \\ u_y \end{bmatrix} \quad \text{Equation (13)}$$

where:

$$\dot{\psi}_i = u_{iz} \quad \text{Equation (14)}$$

Enforcing the concentric constraint $\dot{p}_i = \dot{p} \forall i$ and defining $m = \sum_{i=1}^{n} m_i$, $n = \sum_{i=1}^{n} n_i$, $f = \sum_{i=1}^{n} f_i$, and $f = \sum_{i=1}^{n} f_i$, you get:

$$\dot{n} + f = 0 \quad \text{Equation (15)}$$

$$\dot{m} + \dot{p} \times n + 1 = 0 \quad \text{Equation (16)}$$

and from the above definitions the following can be algebraically derived:

$$u_{xy} = \left( \sum_{i=1}^{n} R_{\psi i} K_{bi} R_{\psi i}^T \right)^{-1} \left( \sum_{i=1}^{n} R_{\psi i} K_{bi} u_i^* + \begin{bmatrix} m_x \\ m_y \end{bmatrix} \right) \quad \text{Equation (17)}$$

where $K_{bi} = \text{diag}(EI_{xi}, EI_{yi})$, and $m_x$ and $m_y$ are the x and y components of m expressed in the Bishop frame R, i.e. $[m_x \; m_y \; m_z]^T = R^T m$.

The stability of a given solution to the above general boundary value problem can be evaluated using a method based on a criteria adapted from optimal control, namely the "conjugate-point test."

With reference to a case of two tubes with constant Ki and constant precurvatures $k_1$ and $k_2$ about their x axes ($u_i^* = [k_i \; 0 \; 0]^T$), Equation (9) can reduce to:

$$\dot{u}_{iz} = \frac{1}{GJ_i} ((EI_{ix} - EI_{iy}) u_{ix} u_{iy} - EI_{ix} k_i u_{iy}) \quad \text{Equation (18)}$$

and the differential equation governing the relative tube angle $\theta = \psi_2 - \psi_1$ can thus be expressed as:

$$\ddot{\theta} = K^T A(\theta) \kappa \sin\theta \quad \text{Equation (19)}$$

where $K = [\kappa_1 \; \kappa_2]^T$, and the matrix $A(\theta)$ is given by:

$$A(\theta) = \frac{(\gamma_1 + \gamma_2) \begin{bmatrix} x_1 x_2 + x_1 \gamma_1 & (x_1 \gamma_2 - x_1 x_2) c_\theta \\ (x_2 \gamma_1 - x_1 x_2) c_\theta & x_1 x_2 + x_2 \gamma_2 \end{bmatrix}^T}{\frac{\mu_1 \mu_2}{\mu_1 + \mu_2} \begin{vmatrix} x_1 + \gamma_2 & (x_1 - \gamma_1) c_\theta \\ (x_2 - \gamma_2) c_\theta & x_2 + \gamma_1 \end{vmatrix}^2} \quad \text{Equation (20)}$$

where $C_\theta = \cos\theta$, and the following symbols for notational compactness are defined as:

$$x_i = EI_{ix} \gamma_1 = EI_{iy} \mu_i = GJ_i \quad \text{Equation (21)}$$

The boundary conditions of Equation (19) are $\theta(0) = \theta_0$, and $\dot{\theta}(L) = 0$.

The stability of a particular configuration can be evaluated numerically by computing the solution h(s) of the variational equation along any solution curve $\theta(s)$. The function h(s) is associated with a solution $\theta(s)$ as follows:

$$\ddot{h}(s) = \frac{\delta}{\delta\alpha} \{ K^T A(\alpha) K \sin\alpha \}_{\alpha=\theta(s)} h(s) \quad \text{Equation (22)}$$

$$h(L) = 1 \quad \text{Equation (23)}$$

$$\dot{h}(L) = 0 \quad \text{Equation (24)}$$

The solution $\theta(s)$ can be stable if the associated h(s) satisfies:

$$h(s) > 0 \forall s \in [0 L] \quad \text{Equation (25)}$$

(i.e., there are no conjugate points). Physically, this condition means that positive variations in the angle at the distal end of the device correspond only to positive variations in angle along the entire length of the device. Graphically, $$h(0) = \frac{d\theta_O}{d\theta_L}$$

is the inverse of the slope of the curve at a point $(\theta_0, \theta_L)$ on the locus of static equilibria as shown in FIGS. 4 and 5A-5D. And energetically, if the condition holds, the system energy is locally positive definite around the static equilibrium with regard to variations in $\theta(s)$.

For any numerically evaluated solution $\theta(s)$, stability numerically can be evaluated, and tests may be performed to show the entire rotation space is stable by sampling $\theta_L \in [0 \; 2\pi]^T$ with sufficient resolution.

It will be noted that $\theta(s) = \pi$ is a stationary solution to Equation (19). Intuitively, this solution can be important to analyze because, in the case of flexurally symmetric tubes, it is the first configuration to become unstable as the overlapped bending angle increases. It also admits a tractable solution and insight into the stability of the flexurally asymmetric case. Applying Equation (22-24) gives:

$$\ddot{h} = -k^T A(\pi) k h = -Ch \quad \text{Equation (26)}$$

where:

$$A(\pi) = \frac{(\mu_1 + \mu_2) \begin{bmatrix} x_1 x_2 + x_1 \gamma_1 \\ x_1 x_2 - x_2 \gamma_1 \end{bmatrix} \begin{bmatrix} x_1 x_2 - x_1 \gamma_2 \\ x_1 x_2 + x_2 \gamma_2 \end{bmatrix}}{\mu_1 \mu_2 (x_1 + x_2)^2 (\gamma_1 + \gamma_2)} \quad \text{Equation (27)}$$

Thus the scalar constant $C = k^T A(\pi) k$, can be a generalization of a constant c, extended to the asymmetric tube case. The conjugate point stability condition then gives:

$$L^2 C < \frac{\pi^2}{4} \quad \text{Equation (28)}$$

Of course, in the case of symmetric stiffness, this condition reduces to the prior result in Equation (1).

If the idealized case of two identical tubes with asymmetric rigidities $EI_x$, $EI_y$, GJ, and precurvatures $\kappa$ are examined then Equation (19) reduces to $$\ddot{\theta} = \frac{4(EI_x^2)(EI_y) k^2 \sin\theta}{GJ(EI_x + EI_y + (EI_x - EI_y) \cos\theta)^2} \quad \text{Equation (29)}$$

And Equation (28) reduces to:

$$k^2 L^2 \left(\frac{EI_x}{GJ}\right)\left(\frac{EI_x}{EI_y}\right) < \frac{\pi^2}{4} \quad \text{Equation (30)}$$

This result provides a more nuanced understanding of stability than the well-established stability condition from Equation (3). Considering the conventional strategy of reducing EI relative to GJ, Equation (30) reveals that only the $EI_x$ reduction is helping to stabilize the device, and, contrary to prior concentric tube steerable device knowledge and practice, reducing $EI_y$ actually worsens the stability. It is observed that decreasing the flexural rigidity ratio $$\frac{EI_x}{EI_y}$$

actually increases stability, making the overall stability condition proportional to $EI_x^2$. Thus Equation (30) suggests that a much more efficient strategy for improving CTR stability while maintaining device strength is to attempt to reduce $EI_x$ alone while preserving both $EI_y$ and GJ as much as possible. As discussed above, further advantages of this strategy include Equation (1) that it is generally easier to preserve GJ than when reducing EI overall, and Equation (2) maintaining a high $EI_y$ preserves more of the device's out-of-plane load capacity.

In practice, the various reductions in $EI_x$, $EI_y$, and GJ will be coupled and dependent on the pattern of removed material, and the tubes will not be identical. Thus, the simple result Equation (30) may be used as an intuitive heuristic to evaluate and improve the design of a single tube's material removal pattern, while using the exact general conditions Equation (28) and Equation (25) to formally evaluate the stability of a full device design.

Example Concentric Tube Steerable Device

FIG. 1 illustrates a concentric tube steerable device 100 that includes a tube 102 having asymmetric flexural rigidity. The device 100 includes of a plurality of tubes 102, 104, 106 having a nested, concentric configuration, and a tube manipulator 108. Although the device 100 is illustrated as having only three tubes 102, 104, 106, it will be understood that the device 100 can include fewer, more, or different sized tubes, as desired.

The tube manipulator 108 can be configured to cause rotation and/or translation of one or more of the tubes 102, 104, 106. In some cases, the tube manipulator 108 includes at least one actuator 107 for rotating at least one tube of the plurality of tubes about a respective tube axis. In some cases, the tube manipulator 108 includes at least one translator 109 for translating at least one tube of the plurality of tubes along a respective tube axis.

The tubes 102, 104, 106 can include one or more straight portions and/or one or more curved portions. In some cases, the tubes 102 are precurved. The precurvature(s) of the tube(s) 102 can vary across embodiments and can be selected to provide a desired rotation space. In some cases, a tube can include two or more different curves, or a curve with nonconstant curvature, such as an elliptical segment, or a helix. Furthermore, in some cases, the precurvature can vary along a length of the tube (e.g., helical pattern).

The tubes 102, 104, 106 can be concentric, hollow, and/or nested tubes. For example, as shown, the tube 104 is an outer tube relative to tube 106 and tube 106 is an inner tube relative to tube 104. In this example, the tube 106 extends coaxially within the tube 104. In addition, the tube 106 terminates at a distal tip 107. A pose of the distal tip 107 can be effectuated through individual or collective rotation or translation of the plurality of tubes 102, 104, 106 about a longitudinal axis. For example, as the tubes 102, 104, 106 interact with one another through relative translational and/or rotational movement, they can cause one another to bend and/or twist, with the tubes 102, 104, and 106, collectively assuming a family of curves.

Furthermore, the tubes 102, 104, 106 can be coaxial in nature such that an axis of tubes (sometimes referred to as a longitudinal axis of the device 100) can be considered to be centered within and follow the curved configuration of the tubes 102, 104, 106. The tubes 102 can be made of elastic or one or more other materials.

The tubes 102, 104, 106 can, individually or in combination, be rotated about a longitudinal axis of the device 100 (e.g., as shown by arrows 112) or can be translated along a longitudinal axis of the device 100 (e.g., as shown by arrows 114). Through translational movement, the tubes 102, 104, 106 can be retracted into one another or extended from one another. As the tubes 102, 104, 106 interact with one another through relative translational and/or rotational movement, they can cause one another to bend and/or twist, with the tubes 102, 104, 106 collectively assuming a family of curves.

In some cases, at least one tube of the device 100 can include structural characteristics 120 that introduce asymmetric flexural rigidities into the respective tube and/or the device 100. In the illustrated example of FIG. 1, only tube 102 is illustrated as having structural modifications 120 that introduce asymmetric flexural rigidity into the tube 102. However, it will be understood that more or different tubes, such as any combination of tubes 102, 104, or 106 may have similar (or different) structural modifications that introduce asymmetric flexural rigidity.

In the illustrated example of FIG. 1, the structural modification 120 to tube 102 include a plurality of slots that are strategically located to weaken the flexural rigidities of the tube 102B in an asymmetric matter. The cut pattern of the slots can create asymmetric stiffness properties in the tube 102. In particular, in this example, the cut pattern of the slots of tube 102 reduces the flexural rigidity about the axis of precurvature ($EI_x$) more than the flexural rigidity perpendicular to the precurvature axis ($EI_y$). It will be understood that the size, location, shape, orientation, number, etc. of the slots can vary across embodiments, as described in more detail herein. Furthermore, it will be understood that slots are merely an example of structural modification that may be utilized, and different or additional structural modification may be used, depending on the embodiments. For example, one or more portions of a tube may include a relatively more flexible material, while one or more other portions made include a relatively less flexible material, so as to introduce asymmetrical flexural rigidities into the tube. As another example, one or more portions of a tube may include a relatively thicker area of material, while one or more other portions made a relatively thinner area of the material (e.g., etching). As another example, in some cases, one or more structural modifications can be implemented to strategically strengthen $EI_y$, while concurrently weakening $EI_x$, maintaining $EI_x$, or strengthening $EI_x$ less than $EI_y$.

Figure 2:
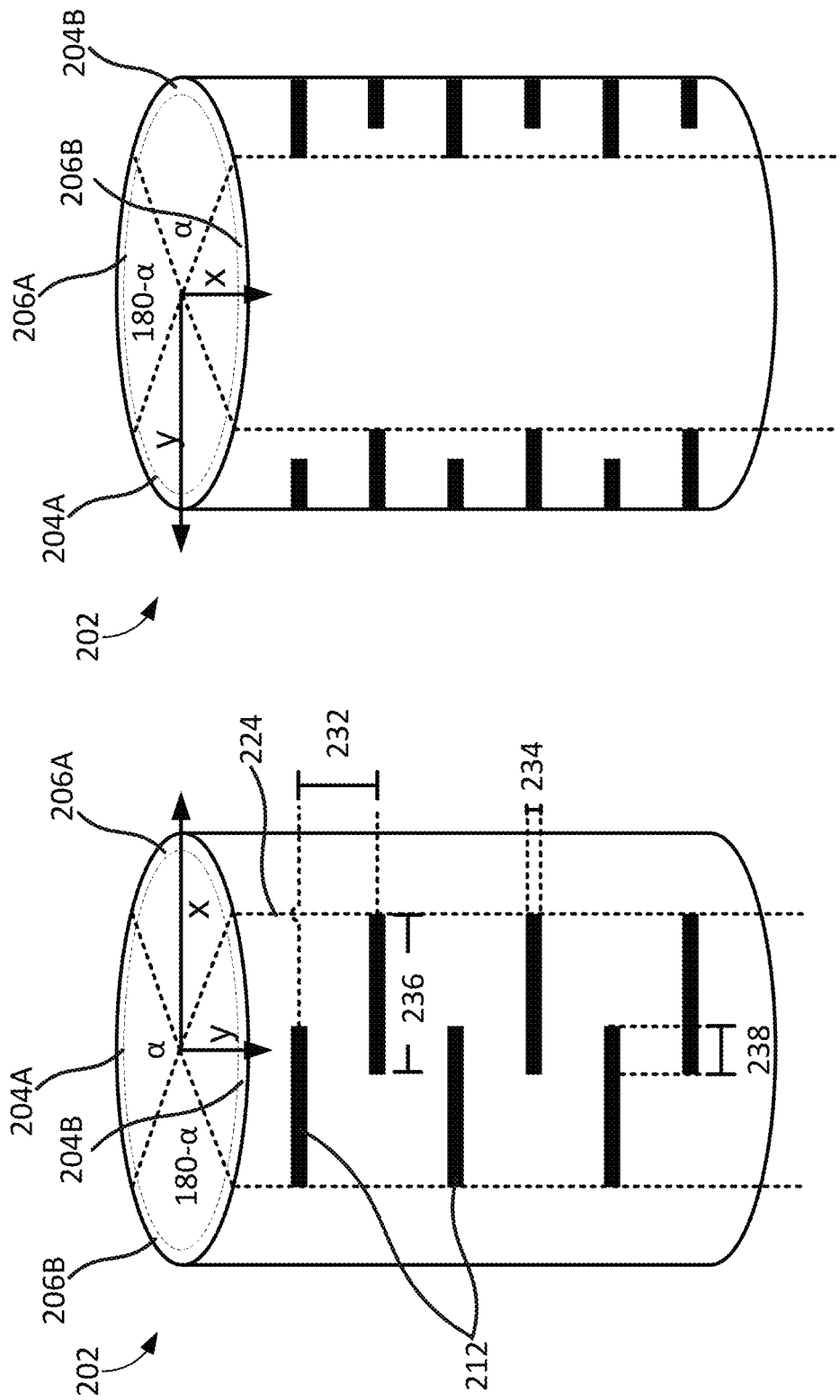
FIGS. 2A and 2B illustrate a side perspective views of an example tube of a concentric tube steerable device.

FIGS. 2A and 2B illustrate a side perspective views of an example tube 202 of a concentric tube steerable device, such as the concentric tube steerable device 100 of FIG. 1. The tube 202 can be an embodiment of the tube 102 of FIG. 1. Although illustrated as a straight tube, for purposes of this example, the tube 200 is precurved about the x-axis. In this way, the axis of precurvature corresponds to the x-axis, and the y-axis corresponds to a second axis that is perpendicular to the precurvature axis.

As shown, the tube 202 is cylindrical in shape. For ease of description, the tube 202 is separated into quadrants 204A, 204B, 206A, and 206B. In this example, the includes structural characteristics in quadrants 204A, 204B that introduce asymmetrical flexural rigidities into the tube 202. In this example, the structural characteristics include the presence of a plurality of slots 212. However, it will be understood that the structural characteristics can vary across embodiments. For example, the structural characteristics can include a combination of one or more of slots, different thickness in material, different materials, etc.

Figure 3:
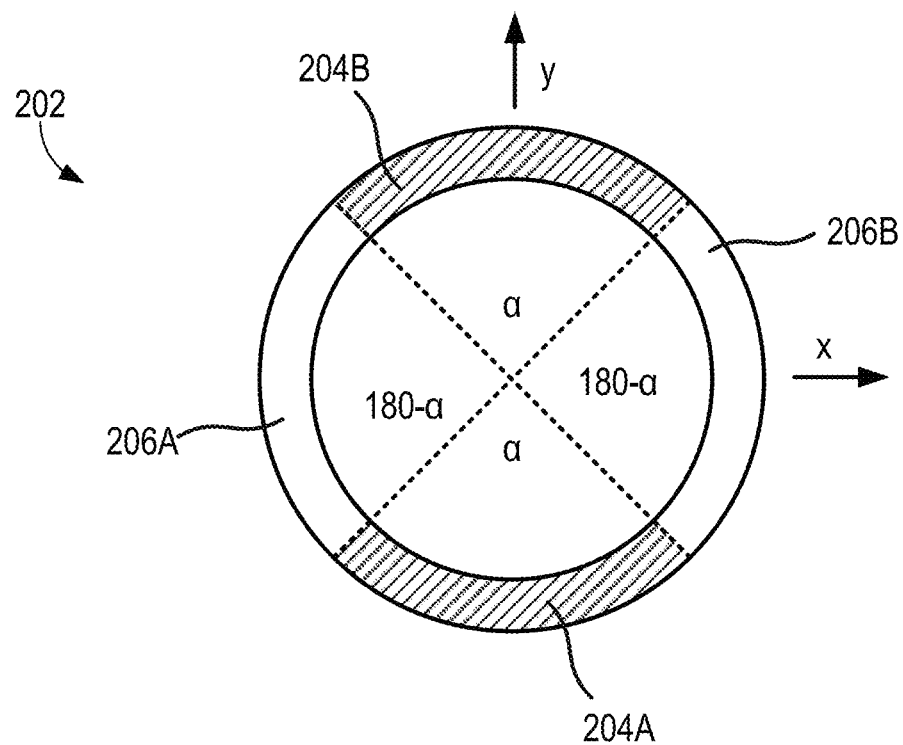
FIG. 3 illustrates a pictorial representation of a top cross-sectional view of the tube of FIGS. 2A and 2B.

In this example, the slots 212 were made in accordance with a cut pattern that reduces the flexural rigidity about the axis of precurvature more than the rigidity perpendicular to the axis of precurvature. In particular, the cut pattern includes a plurality of slots 202 that are evenly distributed along a length of the tube 202 and are offset from one to the next along a length of the tube. It will be understood that FIG. 2A merely illustrates an example cut pattern, and other patterns may be used. For example, in some cases, the distance 232 between slots may vary amongst the slots. As another example, in some cases, the width 234, length 236, or overlap 238, of the slots 212 may be adjusted to achieve desired ratio of asymmetrical flexural rigidities. Furthermore, the angle, $\alpha$, of the "cut region" may vary across embodiments. As a corollary, the "uncut" region is defined as having an angle, 180-$\alpha$, which may vary across embodiments FIG. 3 illustrates a pictorial representation of a top cross-sectional view of the tube 202 of FIGS. 2A and 2B. In this example, the shaded portions 204A, 204B correspond to the "cut regions" which correspond to the entire area at includes at least a portion of a slot 212.

As described herein, the presence of the slots selectively weakens the tube's flexural rigidities in an asymmetric manner by reducing the flexural rigidity about the axis of precurvature more than the rigidity perpendicular to the precurvature axis.

Figure 4:
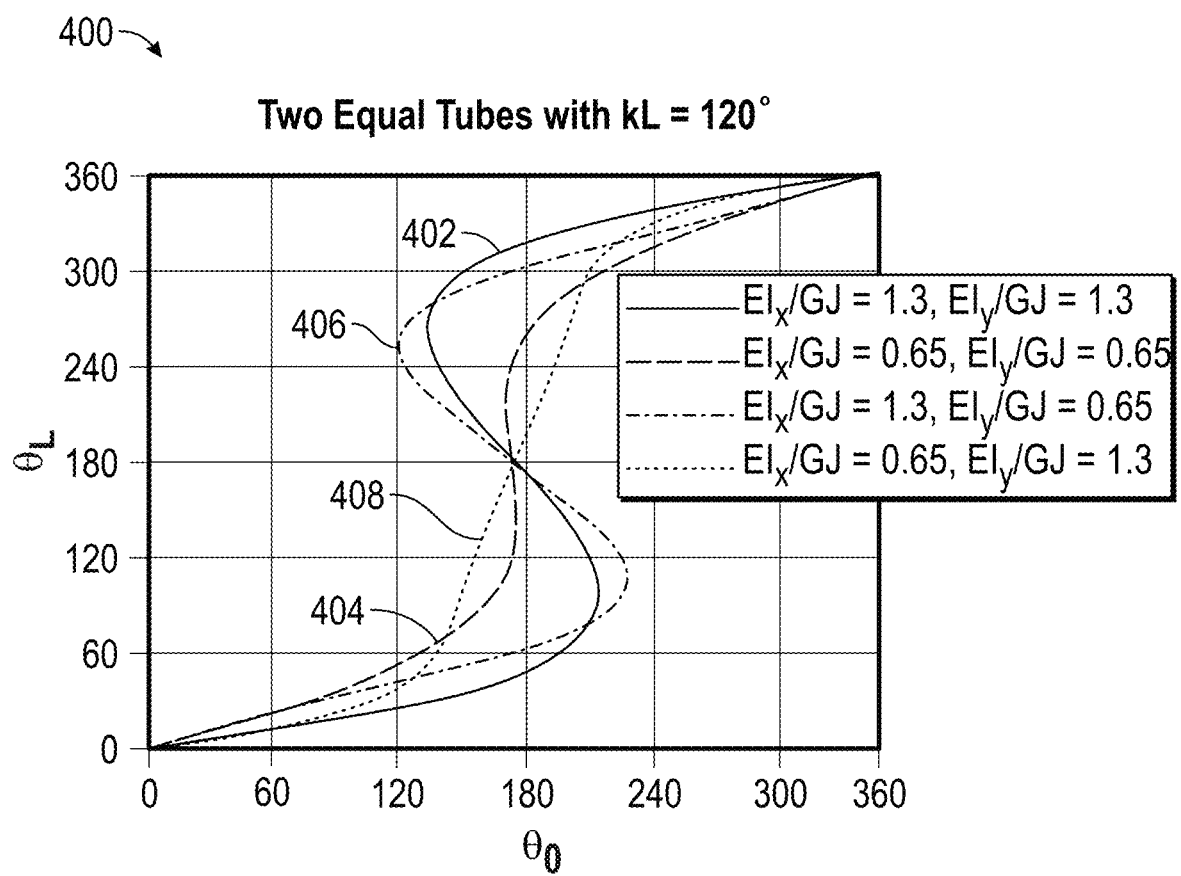
FIG. 4 is a graph illustrating input-output angle curves for a two-tube steerable device with both tubes precurved about the x-axis to a 120° bending angle.

FIG. 4 is a graph 400 illustrating input-output angle curves 402, 404, 406, 408 for a two-tube steerable device with both tubes precurved about the x-axis to a 120° bending angle. The effect of various changes to $EI_x$ and $EI_y$ are shown while holding GJ constant. Reducing $EI_x$ while preserving $EI_y$ and GJ (i.e., curve 408) is shown to be a strong strategy.

The curves 402, 404, 406, 408 in FIG. 4 illustrate the input-to-output angle mapping ($\theta_L$ vs. $\theta_0$) for four different two-tube steerable device designs with two equal tubes, by solving Equation (19) with $\dot{\theta}(L)=0$. The precurvatures of the tubes are such that the total bending angle, $\kappa L$, is 120° when the tubes are aligned (an extreme case). The nominal case has tubes with symmetric bending stiffness and $$\frac{EI}{GJ} = 1.3,$$

which is consistent with solid tube walls and a Poisson's ratio of $v=0.3$.

The regions of the plot with a negative value of $$h = \frac{d\theta_0}{d\theta_L}$$

(the reciprocal of the slope of the graph) represent unstable configurations, and the minimum value of h over the whole curve is a metric for stability of the configuration space. The value of IA in the nominal unmodified tube case is about 2.3 times larger than the maximum value for a stable configuration space, $\pi^2/4$. The curve 404, having $$\frac{EI_x}{GJ} = .65 \text{ and } \frac{EI_y}{GJ} = .65,$$

shows that an "almost stable" workspace can be achieved by reducing EI/GJ uniformly to half its previous value, but the instability around $\theta=\pi$ remains, and it is difficult to achieve such a reduction without dramatically reducing the overall flexural rigidity. The curve 406, having $$\frac{EI_x}{GJ} 1.3 \text{ and } \frac{EI_y}{GJ} = .65,$$

shows that reducing $$\frac{EI_y}{GJ}$$

alone actually makes the instability worse than the nominal case. Finally, the curve 408, having $$\frac{EI_x}{GJ} = .65 \text{ and } \frac{EI_y}{GJ} = 1.3,$$

shows that reducing $$\frac{EI_x}{GJ}$$

alone improves stability even more than the same amount of uniform reduction, creating a stable workspace while also preserving much of the original stiffness.

Above, the stability of the $\theta(s)=\pi$ configuration of the two-tube case was analyzed, and, thus, qualitatively examining the entire rotation space in an example case. The analysis clearly illustrates that reducing bending stiffness in only one direction (about the axis of precurvature) is a strong strategy for improving the stability of $\theta(s)=\pi$.

FIGS. 5A-5D are graphs illustrating input-output angle curves for a two-tube steerable device with equal tubes having $$\frac{EI_y}{GJ} = 1.3.$$

The effect of reducing only $EI_x$ is shown for four different cases of bending angle κL.

Figure 5A:
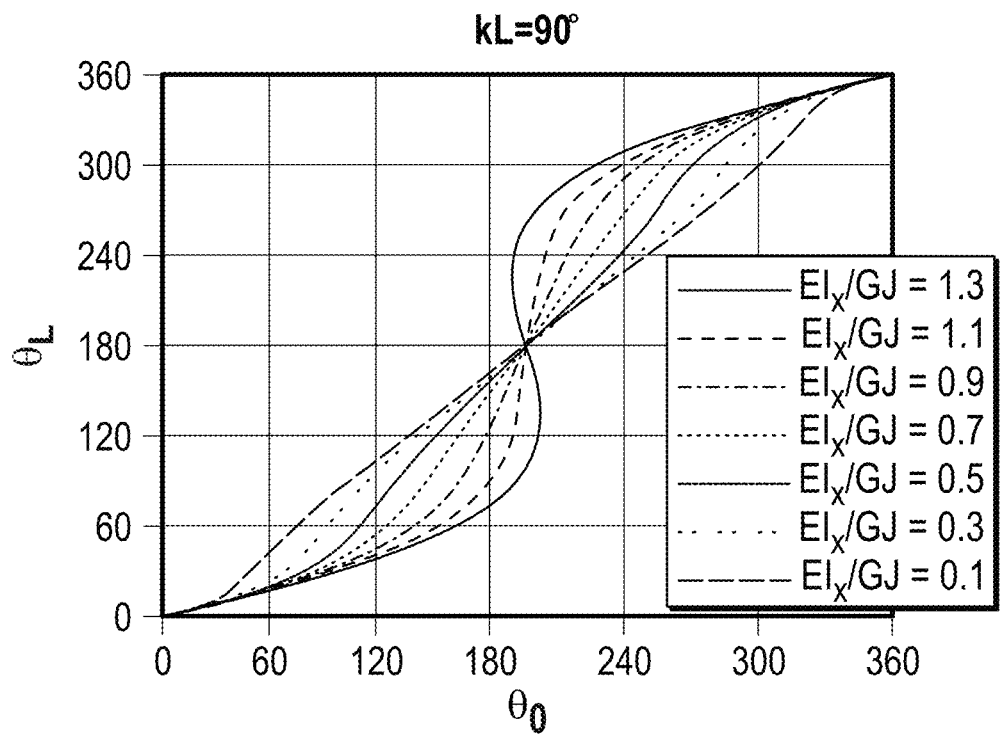
FIGS. 5A-5D are graphs illustrating input-output angle curves for a two-tube steerable device with equal tubes.
Figure 5B:
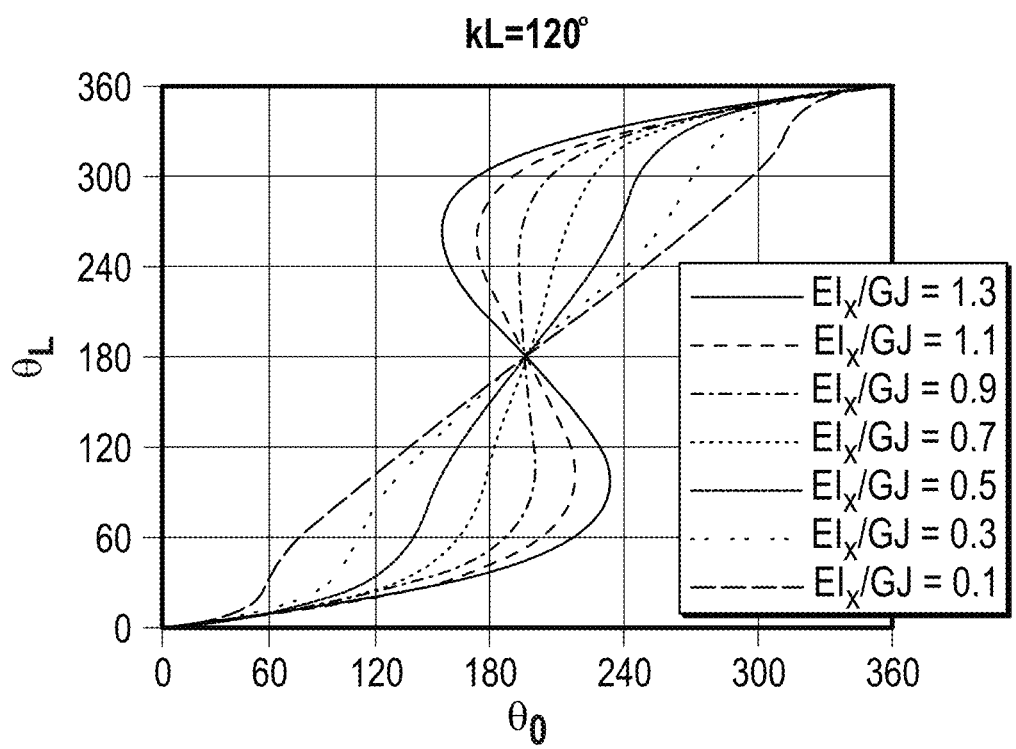
Figure 5C:
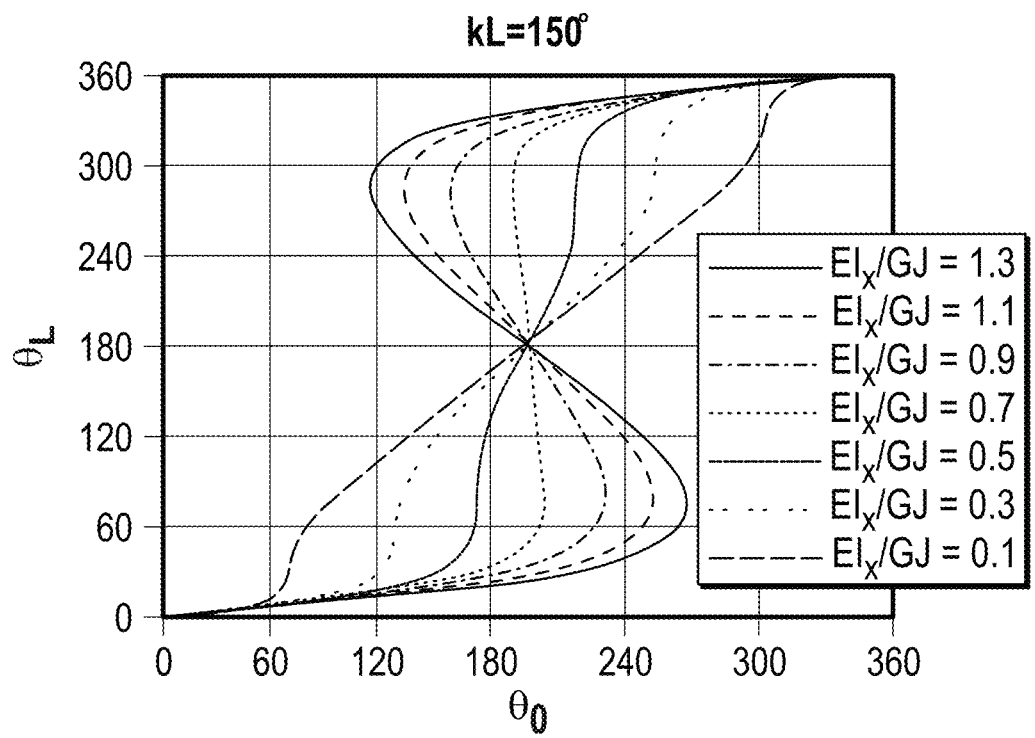
Figure 5D:
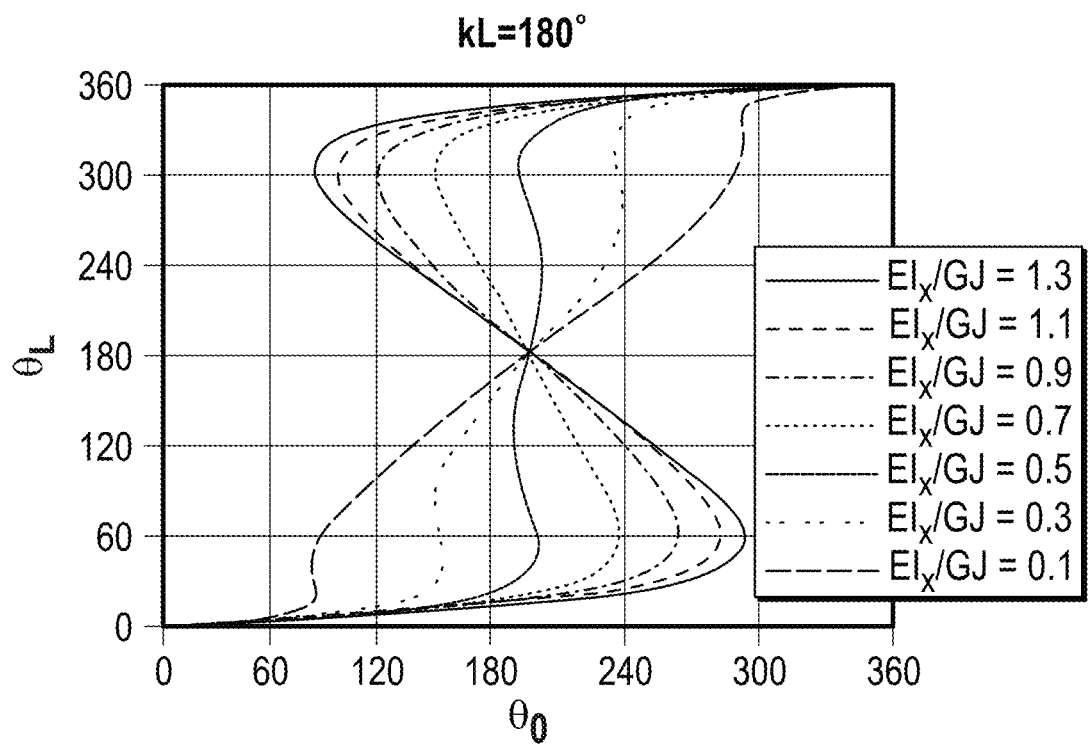

Referring to FIGS. 5A-5D, this phenomenon is illustrated for a pair of equal tubes with constant $$\frac{EI_y}{GJ}$$

over a range of stiffness asymmetry $$\frac{EI_x}{EI_y}.$$

in particular, FIGS. 5A and 5B show that for a total bending angle of 120° (or less), the tube pair can be stabilized by reducing $EI_x$ alone, and stability of the θ=180° configuration implies stability of the entire rotation space. However, the FIGS. 5C and 5D illustrate that for larger bending angles, instabilities (negative slope regions) are possible at other configurations even when e(s)=180° is stable. Indeed, in the kL=180° case, the curves are unstable regardless of $EI_x$. In such extreme cases, stability could be improved by some combination of $EI_x$ and $EI_y$ reduction relative to GJ. But in the most practical cases, stability improvement can be most efficiently gained by reducing $EI_x$ relative to both $EI_y$ and GJ, as shown by FIGS. 5A and 5B.

Benefits of flexural asymmetry in accordance with embodiments of the present inventive concept will now be discussed with respect a prototype two-tube concentric tube steerable device segment. Two Nitinol tubes were used with parameters given in Table I below.

TABLE 1

Example Tube Design Parameters

|  | OD (mm) | ID (mm) | w (mm) | p (mm) | α |
|---|---|---|---|---|---|
| Tube 1 (Outer) | 2.72 | 2.52 | 0.1 | 0.75 | 77° |
| Tube 2 (Inner) | 2.33 | 2.09 | 0.1 | 0.75 | 60° |

The main goal was to significantly improve the workspace stability of a tube pair with L=100 mm and $u_1=u_2=[k\ 0\ 0]^T$, where the precurvature is k=10π/2 m$^{-1}$. A further aim was to produce tubes with equal $EI_x$ so that the balanced stiffness tube pair should be able to execute a full range of bending angles from 0° (straight) to k L=90° (fully curved).

After conducting initial finite element simulations using several possible cut pattern geometries, a cut pattern, such as that shown in FIG. 2A, can efficiently lower $EI_x$ while preserving a significant portion of the original $EI_y$ and GJ.

Figure 6B:
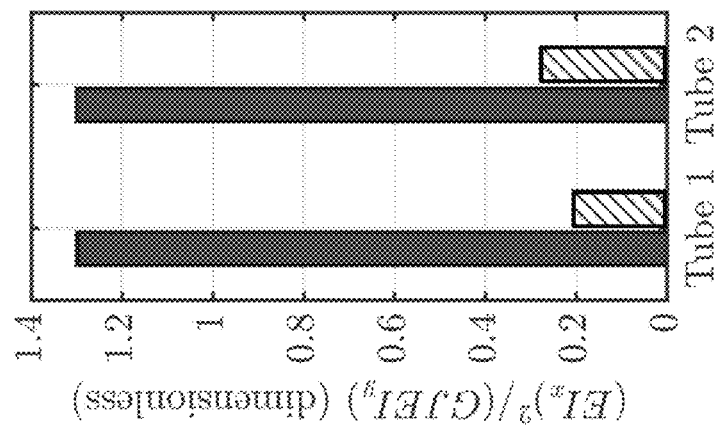
FIG. 6B is a bar chart illustrating a corresponding reduction in the dimensionless stability parameter $L^2C$ for the example tube pair.
Figure 6A:
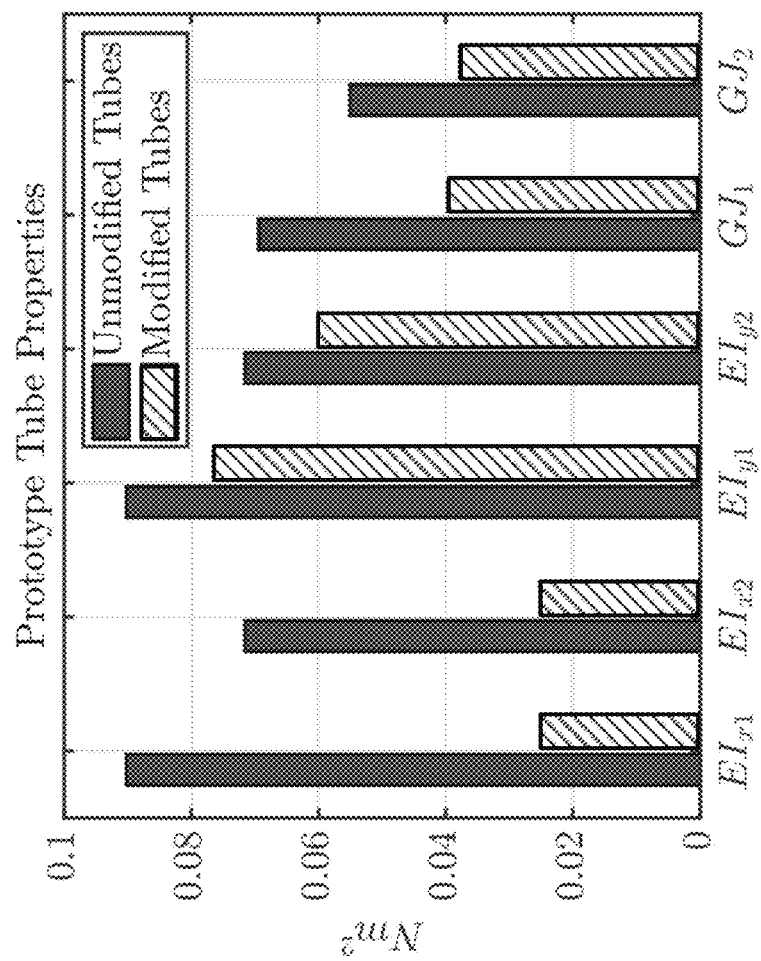
FIG. 6A is a bar chart illustrating the flexural and torsional rigidities of example modified and unmodified tubes.

FIG. 6A is a bar chart illustrating the flexural and torsional rigidities of example modified and unmodified tubes, and FIG. 6B is a bar chart illustrating a corresponding reduction in the dimensionless stability parameter $L^2C$ for the example tube pair.

In this example, for each tube, $EI_x$ is reduced by a greater percentage than either $EI_y$ or GJ. The outer tube design was chosen to exhibit greater reduction so that the tubes would have equal $EI_x$ and form a balanced stiffness pair. The bar chart of FIG. 6B illustrates a corresponding reduction in the dimensionless stability parameter $L^2C$ for this tube pair, calculated from the individual rigidity values by applying Equation (28). Note that the stability is improved by a larger factor than any of the stiffness reductions in the first chart. Thus, the stability improvement is achieved with far less stiffness reduction compared to conventional methods.

Figure 7A:
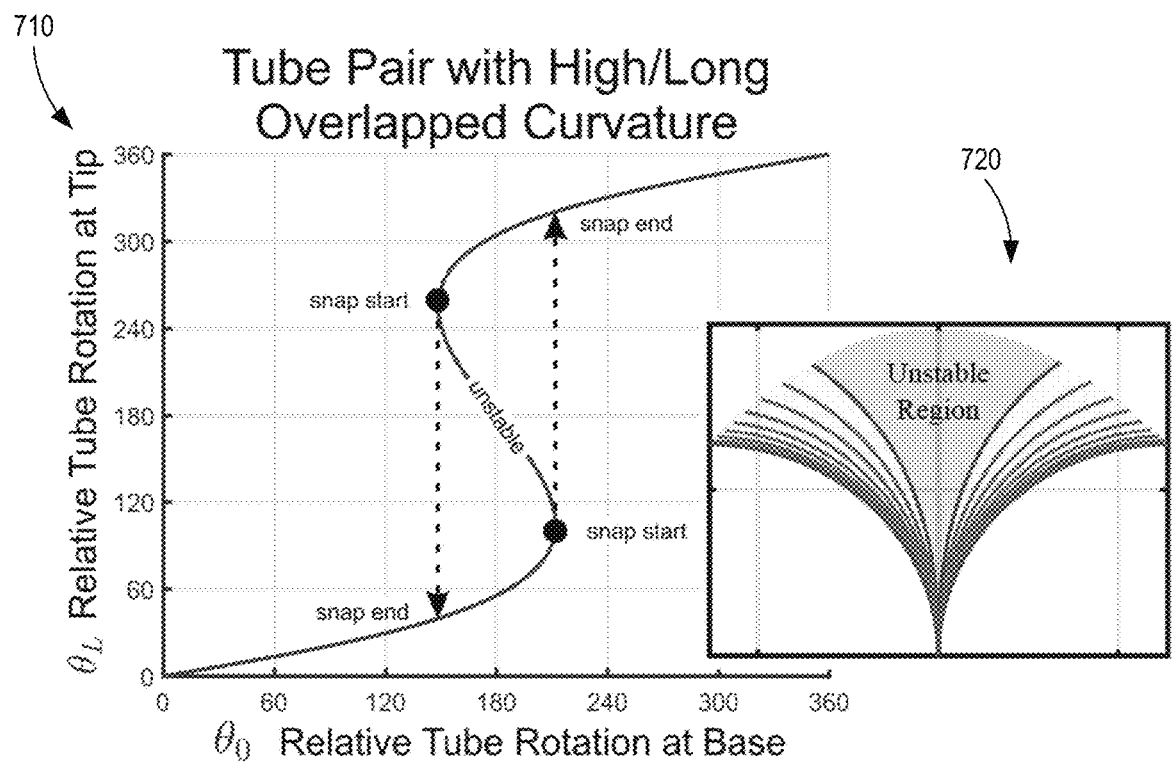
FIG. 7A includes a chart showing an input-output angle curve illustrating various unstable regions, and a plot of an y-z projection of the rotation space of the tubes.
Figure 7B:
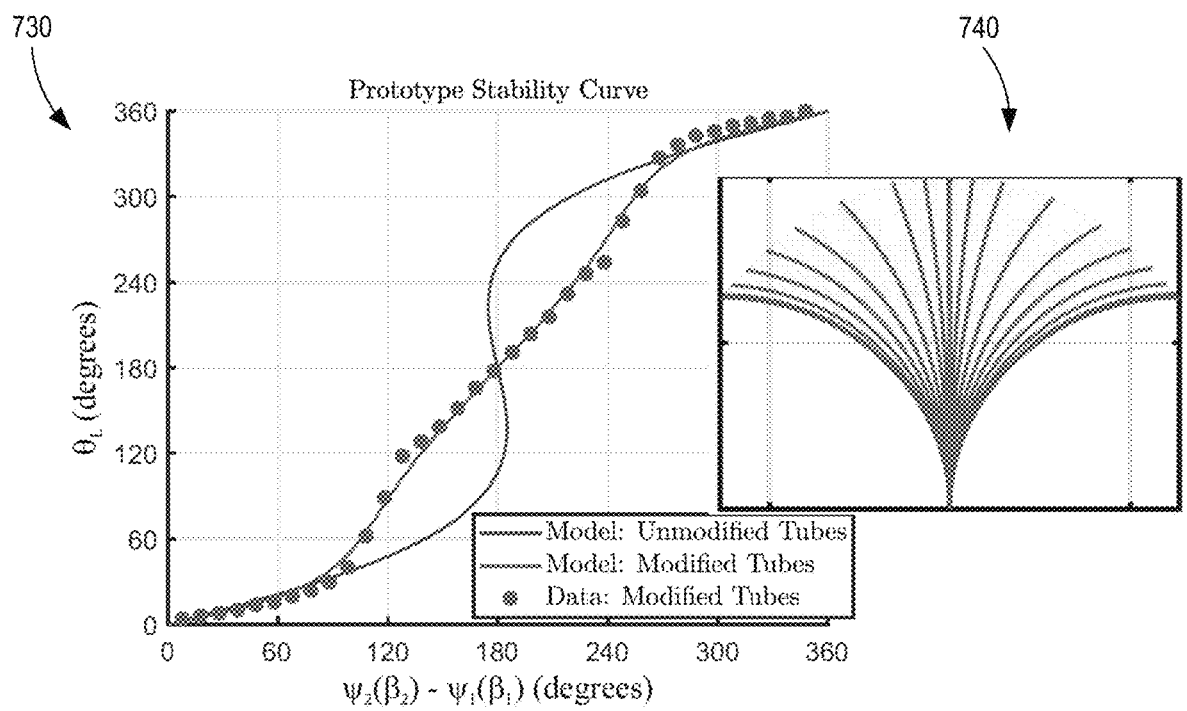
FIG. 7B includes a chart showing input-output angle curve illustrating that the entire rotation space is stabilized by the design disclosed herein, and a plot showing the y-z projection of the rotation space of the tubes.

FIG. 7A includes a chart 710 showing an input-output angle curve illustrating various unstable regions, and a plot 720 of an y-z projection of the rotation space of the tubes. FIG. 7B includes a chart 730 showing input-output angle curve illustrating that the entire rotation space is stabilized by the design disclosed herein, and a plot 740 showing the y-z projection of the rotation space of the tubes. The y-z projection of the configuration space is shown. The full model is solved to obtain the device shape in space as the tubes are rotated by equal 7° increments in opposite directions such that θ ranges from 0° to 360°. Note that while the unmodified pair snaps at θ=185° across the gap (as shown in FIG. 7A), the modified tube pair never snaps (as shown in FIG. 7B), has a more evenly distributed set of configurations, and is able to fully straighten out because the tubes have $EI_{1x}=EI_{2x}$.

As discussed herein, some embodiments of the present inventive concept provide new methods for improving the stability of concentric tube steerable devices by using asymmetric flexural rigidity.

Terminology

Conditional language, such as, among others, "can," "could," "might," or "may," unless specifically stated otherwise, or otherwise understood within the context as used, is generally intended to convey that certain embodiments include, while other embodiments do not include, certain features, elements, and/or steps. Thus, such conditional language is not generally intended to imply that features, elements and/or steps are in any way required for one or more embodiments or that one or more embodiments necessarily include logic for deciding, with or without user input or prompting, whether these features, elements and/or steps are included or are to be performed in any particular embodiment.

Unless the context clearly requires otherwise, throughout the description and the claims, the words "include," "can include," and the like are to be construed in an inclusive sense, as opposed to an exclusive or exhaustive sense; that is to say, in the sense of "including, but not limited to." As used herein, the terms "connected," "coupled," or any variant thereof means any connection or coupling, either direct or indirect, between two or more elements; the coupling or connection between the elements can be physical, logical, or a combination thereof. Additionally, the words "herein," "above," "below," and words of similar import, when used in this application, refer to this application as a whole and not to any particular portions of this application. Where the context permits, words in the above Detailed Description using the singular or plural number may also include the plural or singular number, respectively. The word "or" in reference to a list of two or more items, covers all of the following interpretations of the word: any one of the items in the list, all of the items in the list, and any combination of the items in the list. Likewise the term "and/or" in reference to a list of two or more items, covers all of the following interpretations of the word: any one of the items in the list, all of the items in the list, and any combination of the items in the list.

Depending on the embodiment, certain operations, acts, events, or functions of any of the routines described elsewhere herein can be performed in a different sequence, can be added, merged, or left out altogether (non-limiting example: not all are necessary for the practice of the algorithms). Moreover, in certain embodiments, operations, acts, functions, or events can be performed concurrently, rather than sequentially.

These and other changes can be made to the invention in light of the above Detailed Description. While the above description describes certain examples of the invention, and describes the best mode contemplated, no matter how detailed the above appears in text, the invention can be practiced in many ways. Details of the system may vary considerably in its specific implementation, while still being encompassed by the invention disclosed herein. As noted above, particular terminology used when describing certain features or aspects of the invention should not be taken to imply that the terminology is being redefined herein to be restricted to any specific characteristics, features, or aspects of the invention with which that terminology is associated. In general, the terms used in the following claims should not be construed to limit the invention to the specific examples disclosed in the specification, unless the above Detailed Description section explicitly defines such terms. Accordingly, the actual scope of the invention encompasses not only the disclosed examples, but also all equivalent ways of practicing or implementing the invention under the claims.

Disjunctive language such as the phrase "at least one of X, Y, or Z," unless specifically stated otherwise, is otherwise understood with the context as used in general to present that an item, term, etc., may be either X, Y, or Z, or any combination thereof (non-limiting examples: X, Y, and/or Z). Thus, such disjunctive language is not generally intended to, and should not, imply that certain embodiments require at least one of X, at least one of Y, or at least one of Z to each be present.

Unless otherwise explicitly stated, articles such as "a" or "an" should generally be interpreted to include one or more described items. Accordingly, phrases such as "a device configured to" are intended to include one or more recited devices. Such one or more recited devices can also be collectively configured to carry out the stated recitations. For example, "a processor configured to carry out recitations A, B and C" can include a first processor configured to carry out recitation A working in conjunction with a second processor configured to carry out recitations B and C.

While the above detailed description has shown, described, and pointed out novel features as applied to various embodiments, it can be understood that various omissions, substitutions, and changes in the form and details of the devices or algorithms illustrated can be made without departing from the spirit of the disclosure. As can be recognized, certain embodiments described elsewhere herein can be embodied within a form that does not provide all of the features and benefits set forth herein, as some features can be used or practiced separately from others. The scope of certain embodiments disclosed herein is indicated by the appended claims rather than by the foregoing description. All changes which come within the meaning and range of equivalency of the claims are to be embraced within their scope.

Any terms generally associated with circles, such as "radius" or "radial" or "diameter" or "circumference" or "circumferential" or any derivatives or similar types of terms are intended to be used to designate any corresponding structure in any type of geometry, not just circular structures. For example, "radial" as applied to another geometric structure should be understood to refer to a direction or distance between a location corresponding to a general geometric center of such structure to a perimeter of such structure; "diameter" as applied to another geometric structure should be understood to refer to a cross sectional width of such structure; and "circumference" as applied to another geometric structure should be understood to refer to a perimeter region. Nothing in this specification or drawings should be interpreted to limit these terms to only circles or circular structures.

What is claimed is:

1. A concentric tube steerable device comprising:
a plurality of tubes having a nested, concentric configuration, the plurality of tubes comprising an outer tube and an inner tube that extends coaxially within the outer tube, wherein the inner tube terminates at a distal tip, wherein a pose of the distal tip is effectuated through individual or collective rotation or translation of the plurality of tubes about a tube axis; and
at least one actuator for rotating at least one tube of the plurality of tubes about a respective tube axis and/or translating at least one tube of the plurality of tubes along a respective tube axis,
wherein each tube of the plurality of tubes comprises a precurved portion and corresponding axis of precurvature,
wherein, for each tube of the plurality of tubes, a flexural rigidity of a respective tube along its axis of precurvature is less than a flexural rigidity of the respective tube along a second axis that is perpendicular to the axis of precurvature, and
wherein a ratio of the flexural rigidity along the axis of precurvature to the flexural rigidity along the second axis is less than 0.8.

2. The device of claim 1, wherein the ratio of the flexural rigidity along the axis of precurvature to the flexural rigidity along the second axis is less than or equal to 0.5.

3. The device of claim 1, wherein, for each tube of the plurality of tubes, a ratio of the flexural rigidity along the axis of precurvature squared over a torsional rigidity of the respective tube times the flexural rigidity along the second axis is less than a sum of 1 plus an effective Poisson's ratio of a material of the respective tube.

4. The device of claim 1, wherein a first tube of the plurality of tubes comprises a plurality of slots, wherein a presence of the plurality of slots introduces asymmetric stiffness properties in the first tube, wherein the asymmetric stiffness properties include a lower flexural rigidity of the first tube along its axis of precurvature relative to the flexural rigidity of the first tube along its second axis.

5. The device of claim 4, wherein the plurality of slots includes a first set of slots and a second sets of slots located opposite the first set of slots, wherein each of the plurality of slots is proximate a plane corresponding to the axis of precurvature.

6. The device of claim 4, wherein no slot is located proximate a plane corresponding to the second axis.

7. The device of claim 4, wherein the plurality of slots comprises an interleaved series of slots along a length of the first tube.

8. The device of claim 4, wherein each slot comprises a substantially rectangular shape, and wherein a longest edge of each slot is perpendicular to a longitudinal axis of the first tube.

9. The device of claim 1, wherein first portions of a first tube are thinner than second portions of the first tube, wherein a difference in thickness between the first portions and the second portions introduces asymmetric stiffness properties in the first tube including a reduction in the flexural rigidity of the first tube along its axis of precurvature relative to the flexural rigidity of the first tube along its second axis.

10. The device of claim 9, wherein the first portions are located on opposite facing sides of the first tube, proximate a plane corresponding to the axis of precurvature.

11. The device of claim 1, wherein first portions of a first tube are composed of a first material, wherein second portions of the first tube are composed of a second material, wherein a difference in structural characteristics between the first material and the second material introduces asymmetric stiffness properties in the first tube including a reduction in the flexural rigidity of the first tube along its axis of precurvature relative to the flexural rigidity of the first tube along its second axis.

12. A concentric tube steerable device comprising:
    an outer tube, wherein the outer tube comprises:
        precurved portion, wherein the precurved portion is defined by an axis of precurvature,
        a first plurality of discrete openings distributed along a first side of the outer tube, and
        a second plurality of discrete openings distributed along a second side of the outer tube, wherein the second side is opposite the first side,
        wherein the first plurality of discrete openings and the second plurality of discrete openings introduce asymmetric stiffness properties in the outer tube including a reduction in a flexural rigidity of the outer tube along the axis of precurvature relative to a flexural rigidity of the outer tube along a second axis that is perpendicular to the axis of precurvature, wherein a ratio of the flexural rigidity of the outer tube along the axis of precurvature to the flexural rigidity of the outer tube along the second axis is less than 0.8;
    an inner tube that is nested and extends coaxially within the outer tube, the inner tube terminating at a distal tip, wherein a pose of the distal tip is effectuated through individual or collective rotation or translation of the outer tube and/or the inner tube,
    an actuator for rotating at least one of the outer tube about an outer tube axis or the inner tube about an inner tube axis; and
    a translator for translating at least one of the outer tube along the outer tube axis or the inner tube along the inner tube axis.

13. The device of claim 12, wherein the asymmetric stiffness properties include a reduction in the flexural rigidity of the outer tube along its axis of precurvature relative to a torsional rigidity of the outer tube.

14. The device of claim 12, wherein the precurved portion is a first precurved portion, wherein the axis of precurvature is a first axis of precurvature, wherein the inner tube comprises a second precurved portion, wherein the second precurved portion of the inner tube is defined by a second axis of precurvature, and wherein a ratio of a flexural rigidity of the inner tube along the second axis of precurvature to a flexural rigidity of the inner tube along a third axis that is perpendicular to the second axis of precurvature is less than or equal to 0.5.

15. A concentric tube steerable device, comprising:
    a plurality of tubes having a nested, concentric configuration, the plurality of tubes comprising an outer tube and an inner tube that extends coaxially within the outer tube, wherein the inner tube terminates at a distal tip, wherein a pose of the distal tip is effectuated through individual or collective rotation or translation of the plurality of tubes about a tube axis; and
    at least one actuator for rotating at least one tube of the plurality of tubes about a respective tube axis and/or translating at least one tube of the plurality of tubes along a respective tube axis,
    wherein each tube of the plurality of tubes comprises a precurved portion and corresponding axis of precurvature,
    wherein for each tube of the plurality of tubes:
        a flexural rigidity of a respective tube along its axis of precurvature is less than a flexural rigidity of the respective tube along a second axis that is perpendicular to the axis of precurvature, and
        a ratio of the flexural rigidity along the axis of precurvature squared over a torsional rigidity of the respective tube times the flexural rigidity along the second axis is less than a sum of 1 plus an effective Poisson's ratio of a material of the respective tube.

16. The device of claim 15, wherein the ratio of the flexural rigidity along the axis of precurvature to the flexural rigidity along the second axis is less than 0.8.

17. The device of claim 15, wherein, for each tube of the plurality of tubes, the flexural rigidity of the respective tube along its axis of precurvature is lower than a torsional rigidity of the respective tube.

18. The device of claim 15, wherein a first tube of the plurality of tubes comprises a plurality of slots, wherein a presence of the plurality of slots introduces asymmetric stiffness properties in the first tube including a lower flexural rigidity of the first tube along its axis of precurvature relative to the flexural rigidity of the first tube along its second axis.

19. The device of claim 18, wherein the plurality of slots includes a first set of slots and a second sets of slots are located opposite the first set of slots, wherein each of the plurality of slots is proximate a plane corresponding to the axis of precurvature of the first tube.

* * * * *